(12) United States Patent
Gottlieb et al.

(10) Patent No.: US 9,782,276 B2
(45) Date of Patent: Oct. 10, 2017

(54) SOCKET SYSTEM FOR A PROSTHESIS, PROSTHESIS AND PRODUCTION METHOD

(71) Applicant: OTTO BOCK HEALTHCARE GMBH, Duderstadt (DE)

(72) Inventors: Harald Gottlieb, Jutzenbach (DE); Marco Volkmar, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 0 days.

(21) Appl. No.: 14/355,513

(22) PCT Filed: Oct. 30, 2012

(86) PCT No.: PCT/EP2012/004537
§ 371 (c)(1),
(2) Date: Apr. 30, 2014

(87) PCT Pub. No.: WO2013/064241
PCT Pub. Date: May 10, 2013

(65) Prior Publication Data
US 2014/0324191 A1 Oct. 30, 2014

(30) Foreign Application Priority Data
Nov. 3, 2011 (DE) .................. 10 2011 117 802

(51) Int. Cl.
*A61F 2/80* (2006.01)
*A61F 2/78* (2006.01)
(Continued)

(52) U.S. Cl.
CPC .............. *A61F 2/78* (2013.01); *A61F 2/5046* (2013.01); *A61F 2/76* (2013.01); *A61F 2/80* (2013.01);
(Continued)

(58) Field of Classification Search
CPC .......................... A61F 2/80; A61F 2002/7875
See application file for complete search history.

(56) References Cited

U.S. PATENT DOCUMENTS

| 4,536,898 A | 8/1985 | Palfray |
| 5,163,965 A | 11/1992 | Rasmusson et al. |

(Continued)

FOREIGN PATENT DOCUMENTS

| DE | 20207046 U1 | 10/2002 |
| DE | 60103344 T2 | 6/2005 |

(Continued)

OTHER PUBLICATIONS

PCT International Search Report for PCT International Patent Application No. PCT/EP2012/004537, dated Feb. 5, 2013.

*Primary Examiner* — David H Willse
(74) *Attorney, Agent, or Firm* — Holland & Hart LLP

(57) ABSTRACT

The invention relates to a socket system for a prosthesis. The socket system including a prosthesis socket which has a proximal opening for receiving a residual limb and a distal end and which is made, at least partially, of a first fiber-reinforced plastic. The socket system also includes an adapter element which is arranged on the distal end of the prosthesis socket and is designed in such a manner that a distal prosthesis element can be secured to the adapter element. The adapter element includes a base body which is made, at least partially, of a second fiber-reinforced plastic.

13 Claims, 6 Drawing Sheets

(51) Int. Cl.
*A61F 2/76* (2006.01)
*A61F 2/50* (2006.01)

(52) U.S. Cl.
CPC .......... *A61F 2002/5053* (2013.01); *A61F 2002/5055* (2013.01); *A61F 2002/5083* (2013.01); *A61F 2002/5087* (2013.01); *A61F 2002/5089* (2013.01); *A61F 2002/7605* (2013.01); *A61F 2002/7806* (2013.01)

(56) References Cited

U.S. PATENT DOCUMENTS

| | | | |
|---|---|---|---|
| 5,263,990 | A | 11/1993 | Handal |
| 5,888,232 | A * | 3/1999 | Taylor ............... A61F 2/76 403/87 |
| 5,957,980 | A * | 9/1999 | Houser et al. ............... 623/36 |
| 6,063,125 | A | 5/2000 | Arbogast et al. |
| 6,231,617 | B1 | 5/2001 | Fay |
| 6,454,812 | B1 * | 9/2002 | Laghi ............... 623/36 |
| 8,323,353 | B1 * | 12/2012 | Alley ............... A61F 2/76 623/33 |
| 2004/0158332 | A1 | 8/2004 | Carstens |
| 2004/0199263 | A1 | 10/2004 | Rothschild et al. |
| 2005/0209706 | A1 * | 9/2005 | Warila ............... A61F 2/78 623/33 |
| 2008/0234836 | A1 * | 9/2008 | Taylor ............... A61F 2/5046 623/33 |
| 2010/0042227 | A1 | 2/2010 | Schmidt |
| 2010/0115757 | A1 | 5/2010 | Sacherer |

FOREIGN PATENT DOCUMENTS

| | | |
|---|---|---|
| DE | 102006046928 A1 | 4/2008 |
| DE | 102007005648 A1 | 8/2008 |

* cited by examiner

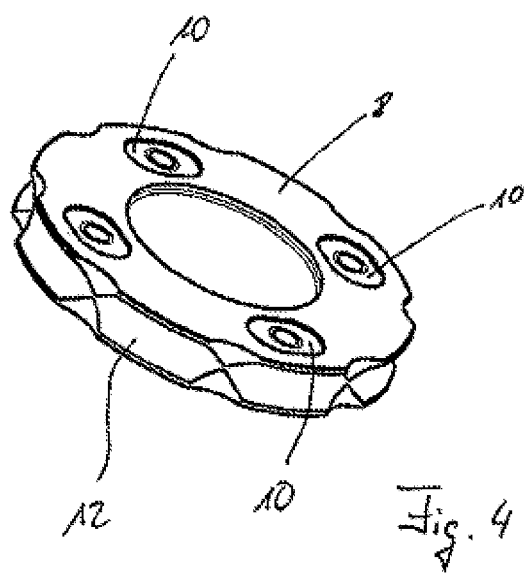

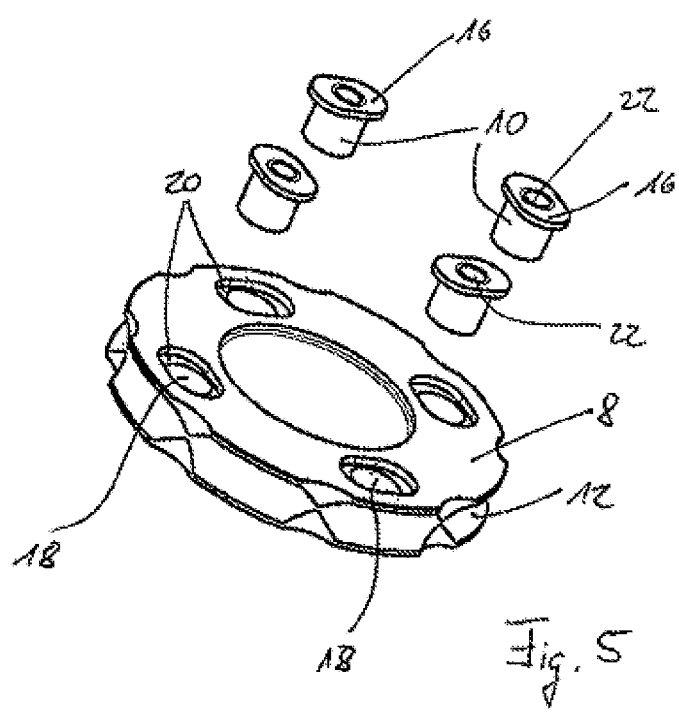

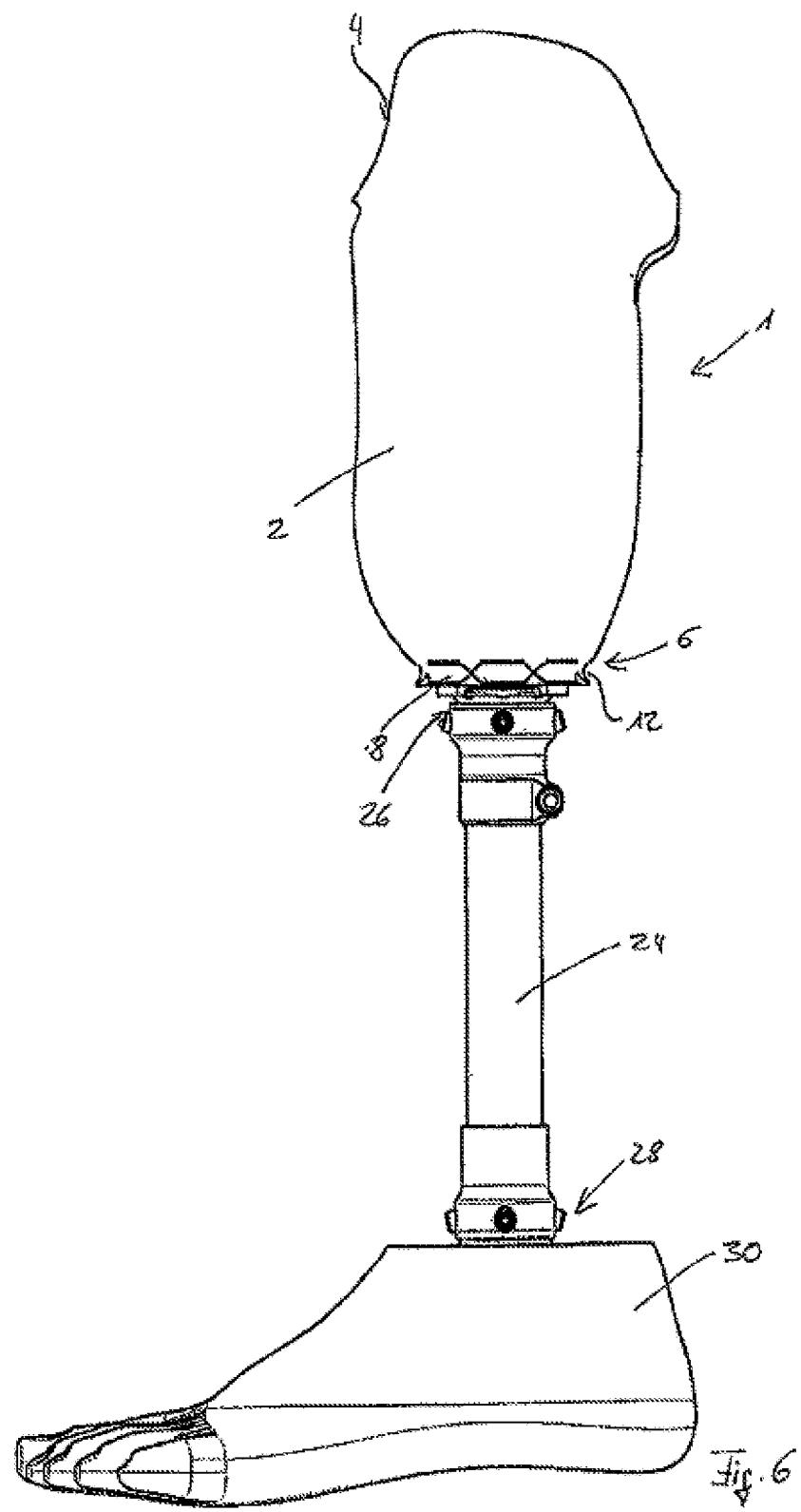

SOCKET SYSTEM FOR A PROSTHESIS, PROSTHESIS AND PRODUCTION METHOD

TECHNICAL FIELD

The invention relates to a socket system for a prosthesis, said socket system comprising a prosthesis socket which has a proximal opening for receiving an amputation stump and a distal end, and which is made at least partially of a first fiber-reinforced plastic, and an adapter element which is arranged on the distal end of the prosthesis socket and is designed in such a way that a distal prosthetic element can be secured on the adapter element. The invention also relates to a production method for such a socket system, and to a prosthesis equipped with such a socket system.

BACKGROUND

Socket systems of this kind are known from the prior art. They have a prosthesis socket, into the proximal end of which an amputation stump of the patient is inserted when the patient is putting on a prosthesis equipped with such a socket system. In order to ensure an optimal hold and fit, and in order to cushion the sometimes sensitive amputation stump, a liner made of an elastic material, for example silicone, can first of all be pulled over the amputation stump. The amputation stump thus provided with the liner is then inserted into the prosthesis socket. As an alternative to this, it is also conceivable to provide cushioning directly on the prosthesis socket and thereby do without the liner or a similar device.

The prosthesis socket also has a distal end, on which distal prosthetic elements can be arranged via an adapter element. These prosthetic elements are generally simulations of amputated limbs, for example of a foot, a lower leg or a hand. Particularly in the case of prosthetic legs, enormous forces sometimes have to be taken up both by the distal prosthetic elements and also by the prosthesis socket, for example during walking with the prosthesis. For this reason, it is necessary that, on the one hand, the prosthesis socket itself is stable and robust and that, on the other hand, a firm and secure connection of the prosthesis socket to the distal prosthetic element is ensured.

In order to ensure the robust and stable configuration of the prosthesis socket, the latter is made at least partially of a first fiber-reinforced plastic. After curing, this fiber-reinforced plastic is robust and stable and, at the same time, light, thereby providing a very pleasant feel when the prosthesis socket is being worn.

In order to ensure a particularly secure connection of the distal prosthetic elements to the prosthesis socket, an adapter element is arranged at the distal end of the prosthesis socket, to which adapter element the distal prosthetic elements can be connected.

A disadvantage is that, despite this elaborate and secure set-up, rattling noises often occur inside a prosthesis, particularly inside a prosthetic leg. This disturbs the wearer of the prosthesis since, for example, walking with the prosthesis is always associated with development of a noise, as a result of which it is also always obvious that the patient is wearing a prosthesis. Moreover, rattling in a prosthetic leg results in a permanent feeling of insecurity, since the patient has the impression that the prosthesis has not been manufactured correctly or has been fitted wrongly. The same also applies of course to prosthetic arms. The level of confidence in the correct function of the prosthesis and, therefore, the self-assurance of the wearer are sometimes greatly affected by this.

SUMMARY

The object of the invention is therefore to propose a socket system for a prosthesis, by means of which the person wearing the prosthesis has greater confidence in the prosthesis, the rattling noise is suppressed and, at the same time, distal prosthetic elements can be attached in a secure and stable manner to the socket system.

The object is achieved, according to the invention, by a socket system of the type in question which is characterized in that the adapter element has a main body which is made at least partially of a second fiber-reinforced plastic.

The invention is based on the recognition that the disturbing rattling noises, which cause the feeling of insecurity, arise because the adapter element, which is produced from aluminum for example in conventional socket systems and prostheses, is able to move relative to the prosthesis socket, since the at least form-fit connection between the two components entails quite considerable play.

This play arises in the process of producing the socket system. Customarily, a mold provided for this purpose, which mold can be individually adapted for example to the amputation stump of the patient, is lined with the first fiber-reinforced plastic in an uncured state. The adapter element is then applied to the position previously measured out on the amputation stump of the patient. This adapter element is made of aluminum, for example, which has the advantage of being easy to work and relatively inexpensive and, additionally, of having a low weight. Thereafter, the first fiber-reinforced plastic, which will later form the prosthesis socket, has to be cured. To do this, the temperature has to be considerably increased. However, since the adapter element and the first fiber-reinforced plastic have different coefficients of thermal expansion, different thermal expansion takes place between the adapter element, made of aluminum for example, and the first fiber-reinforced plastic. The adapter element expands to a greater degree. After the socket system has cooled, both the first fiber-reinforced plastic and also the adapter element contract again. On account of the greater coefficient of thermal expansion of the aluminum, the adapter element contracts to a greater degree than the first fiber-reinforced plastic, which results in play between the adapter element and the prosthesis socket. This leads to the unpleasant and disturbing rattling noise. This surprisingly simple explanation leads to the solution according to the invention, namely that of also designing the adapter element with a main body made of a second fiber-reinforced plastic. In this way, the coefficients of thermal expansion of the first fiber-reinforced plastic, which is intended to form the prosthesis socket, and of the adapter element can be matched, such that play between the adapter element and the cured prosthesis socket no longer occurs upon cooling.

In a conventional casting resin method, the fiber material that is to be sheathed with the plastic is draped onto a positive model of the amputation stump and surrounded by a vacuum hose. The plastics matrix is introduced into the latter under vacuum. During curing, this plastics matrix undergoes an exothermic reaction in a temperature range of ca. 50° C. to 80° C. On account of this relatively low reaction temperature, the thermal expansion in this method is almost negligible, and therefore there is also hardly any appreciable play. By contrast, pre-pregs, i.e. fibers already impregnated with a synthetic resin or a plastic, cure in a temperature range of between 200° C. and 300° C. for example. On account of this much higher temperature, the temperature difference from the temperature range in which the prosthesis socket is intended subsequently to be used is so great that there is considerable thermal expansion and, as a result, clearly noticeable play between the individual components.

Advantageously, the first fiber-reinforced plastic and the second fiber-reinforced plastic contain fibers of the same material. Since extensibility is determined mainly by the material of the fibers, particularly in the event of temperature changes, it is in this way possible to achieve what is in most cases a sufficient adaptation of the coefficients of thermal expansion. Of course, both materials can also comprise the same plastic. This is the simplest and safest way to ensure that both the adapter element and also the prosthesis socket have the same coefficient of thermal expansion, such that it is possible to reliably avoid play between the two components after curing and cooling.

Preferably, the adapter element is connected to the prosthesis socket at least also with cohesive material bonding and/or a form fit. A secure form-fit connection has been made possible by the embodiment according to the invention in which the main body of the adapter element is made of a second fiber-reinforced plastic. In particular, no large undercuts and projections have to be provided to hold the adapter element safely in the intended position with a form fit. It is also possible, by virtue of the embodiment according to the invention, to produce a cohesive material connection to the adapter element during curing of the first fiber-reinforced plastic that forms the prosthesis socket. In this way, a particularly secure attachment of the adapter element to the prosthesis socket is achieved, which is not possible with the material combinations from the prior art.

In a particularly preferred embodiment, the first fiber-reinforced plastic and/or the second fiber-reinforced plastic is a glass-fiber-reinforced or carbon-fiber-reinforced plastic. These materials are easy to work and lead to a particularly high level of stability of the prosthesis socket made from them, and yet they have a very low weight, with the result that a prosthesis socket made at least partially of these materials and the main body of the adapter element made from them ensure a pleasant feel when the prosthesis is being worn, and relatively low loading of the sensitive amputation stump.

Preferably, at least one threaded insert is arranged on the adapter element and is advantageously made of a material not sensitive to water, for example of stainless steel. It is thus possible, in a particularly simple way, to attach distal prosthetic elements to the adapter element. They can simply be screwed into the threaded inserts. If the threaded inserts are produced from a material not sensitive to water, it is possible to produce a socket system, and therefore also a prosthesis, allowing contact with water. In particular, it is possible to produce the socket system and the prosthesis exclusively from components that do not rust and do not suffer other forms of damage upon contact with water. In this way, a prosthesis equipped with a socket system of this kind can also be used, for example, as a bathing prosthesis and does not have to be removed when showering, bathing or swimming, for example. This increases the wearing comfort. Moreover, it is also possible, for example, to design a prosthesis cosmetically, in such a way that the prosthesis wearer cannot be automatically identified as such at first glance, even in a swimming pool.

In a preferred embodiment, the main body of the adapter element has a core made of a fiber-free plastic, which is surrounded by the second fiber-reinforced plastic. It preferably involves the same plastic. In this way, it is possible to cut down in particular on the expensive fiber mats used to produce the fiber-reinforced plastic, and in so doing to reduce the manufacturing costs of the adapter element and, therefore, also of the socket system. Moreover, in the adapter element, it is also possible to use small parts of fiber mats, for example scrap from earlier production steps, for example in order to surround the fiber-free core of the adapter element with them. Of course, the adapter element can also be made entirely of the fiber-reinforced plastic, for which once again small residues of fiber mat, for example scrap from other production steps, can likewise be used. This too reduces the manufacturing costs, since the amount of waste from the expensive fiber mats is reduced. Preferably, the main body of the adapter element is designed as a fiber-reinforced injection-molded part. In special circumstances, the entire adapter element can also be designed as a fiber-reinforced injection-molded part.

A prosthesis according to the invention has an above-described socket system and, therefore, the above-described advantages.

In a method according to the invention for producing a socket system, the following steps in particular are carried out:
sheathing or draping a mold with the first fiber-reinforced plastic in an uncured state,
applying the adapter element made of a second fiber-reinforced plastic, in particular in a cured state, such that the adapter element is in contact with the uncured first fiber-reinforced plastic, and
curing the first fiber-reinforced plastic, such that an at least also form-fit connection is effected between the first fiber-reinforced plastic and the adapter element.

Particularly preferably, when applying the adapter element, the second fiber-reinforced plastic is present in an at least partially uncured state such that, when the first fiber-reinforced plastic cures, an at least also materially cohesive bond is effected between the adapter element and the first fiber-reinforced plastic. In this case, both the first fiber-reinforced plastic and also the second fiber-reinforced plastic are completely cured at the same time in one method step. In method step a), the pre-preg material, i.e. the first fiber-reinforced plastic in the uncured state, is customarily arranged or draped on a positive model of the amputation stump of the patient or on a standard model. The model is usually sheathed with the material.

BRIEF DESCRIPTION OF THE DRAWINGS

An illustrative embodiment of the present invention is explained in more detail below with reference to a drawing, in which:

FIG. 4 shows an adapter element for a socket system according to an illustrative embodiment of the present invention, in a schematic 3D view, FIG. 5 shows the adapter element from FIG. 4 in an exploded view, and FIG. 6 shows a prosthesis according to an illustrative embodiment of the present invention.

DETAILED DESCRIPTION

Figure 1:
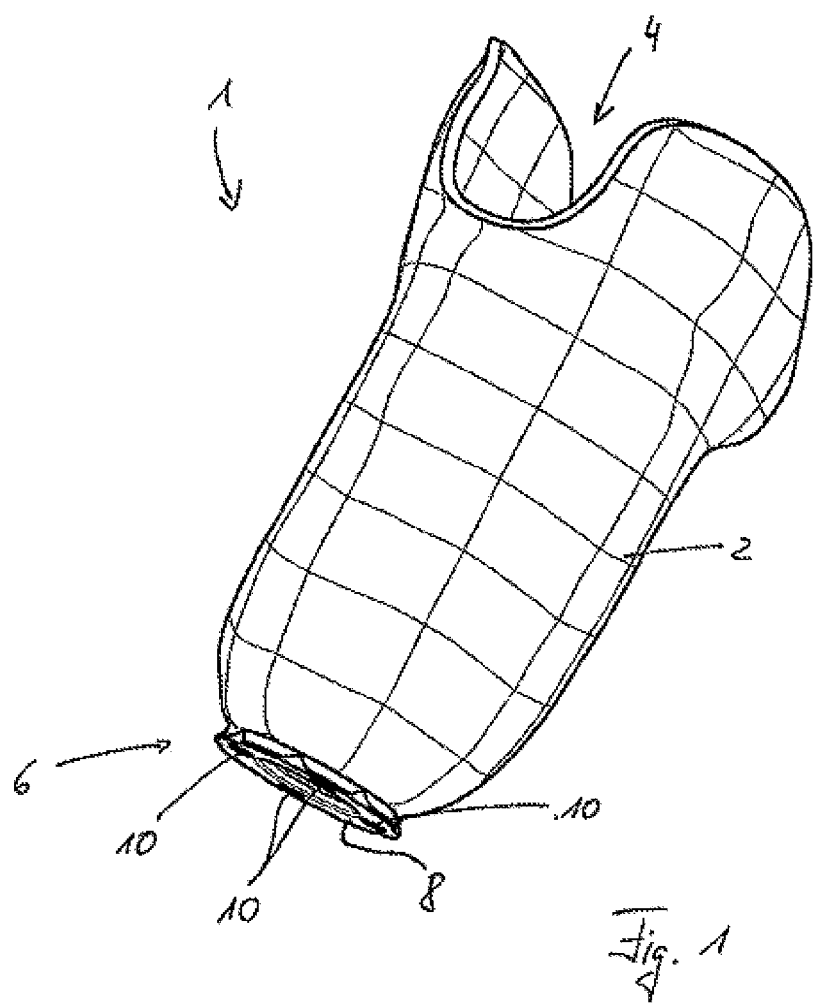
FIG. 1 shows a socket system according to a first illustrative embodiment of the present invention, in a schematic 3D view.

FIG. 1 shows a socket system 1 according to a first illustrative embodiment of the present invention. A prosthesis socket 2 can be seen, which is produced from a first fiber-reinforced plastic. At the upper end of the prosthesis socket 2 in FIG. 1, a proximal opening 4 is shown into which an amputation stump, in this case a below-knee stump, can be inserted.

The prosthesis socket 2 also has a distal end 6, on which an adapter element 8 is arranged. In the illustrative embodiment shown, the prosthesis socket 2 is made entirely of the first fiber-reinforced plastic. Of course, it is also conceivable, for example, to produce only a distal part from the first fiber-reinforced plastic and to produce the rest of the prosthesis socket 2 from a softer or more flexible material, for example. It is also conceivable for the prosthesis socket 2, in the depicted embodiment, to be provided with windows in which, for example, a flexible, elastic or softer material can be provided.

FIG. 1 shows four threaded inserts 10 which are provided on the adapter element 8 and by means of which a distal prosthetic element (not shown) can be connected to the adapter element 8 and thus to the prosthesis socket 2.

Figure 2:
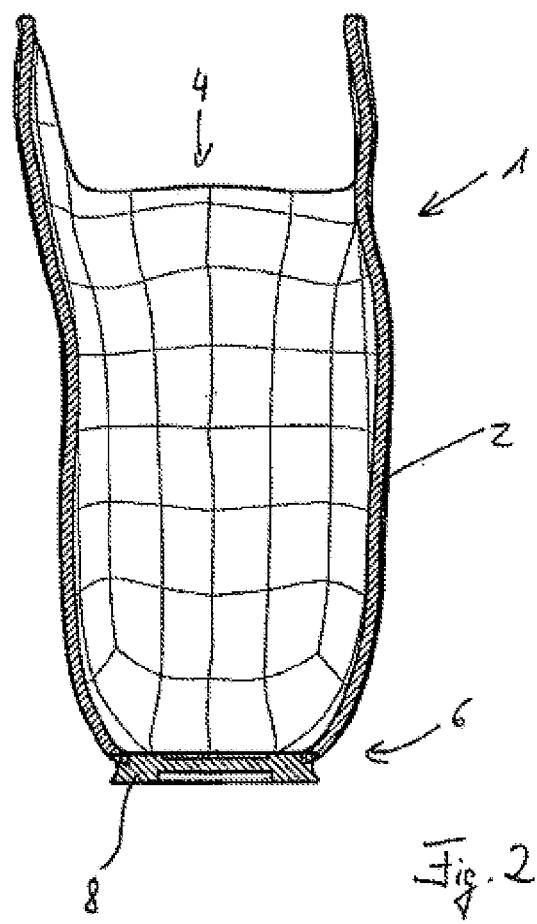
FIG. 2 shows a socket system according to a further illustrative embodiment of the present invention, in a cross-sectional view.

FIG. 2 shows the prosthesis socket 2 in a cross-sectional view. The adapter element 8 is located at the distal end 6 of the prosthesis socket 2. The threaded inserts 10 are not shown in FIG. 2.

Figure 3:
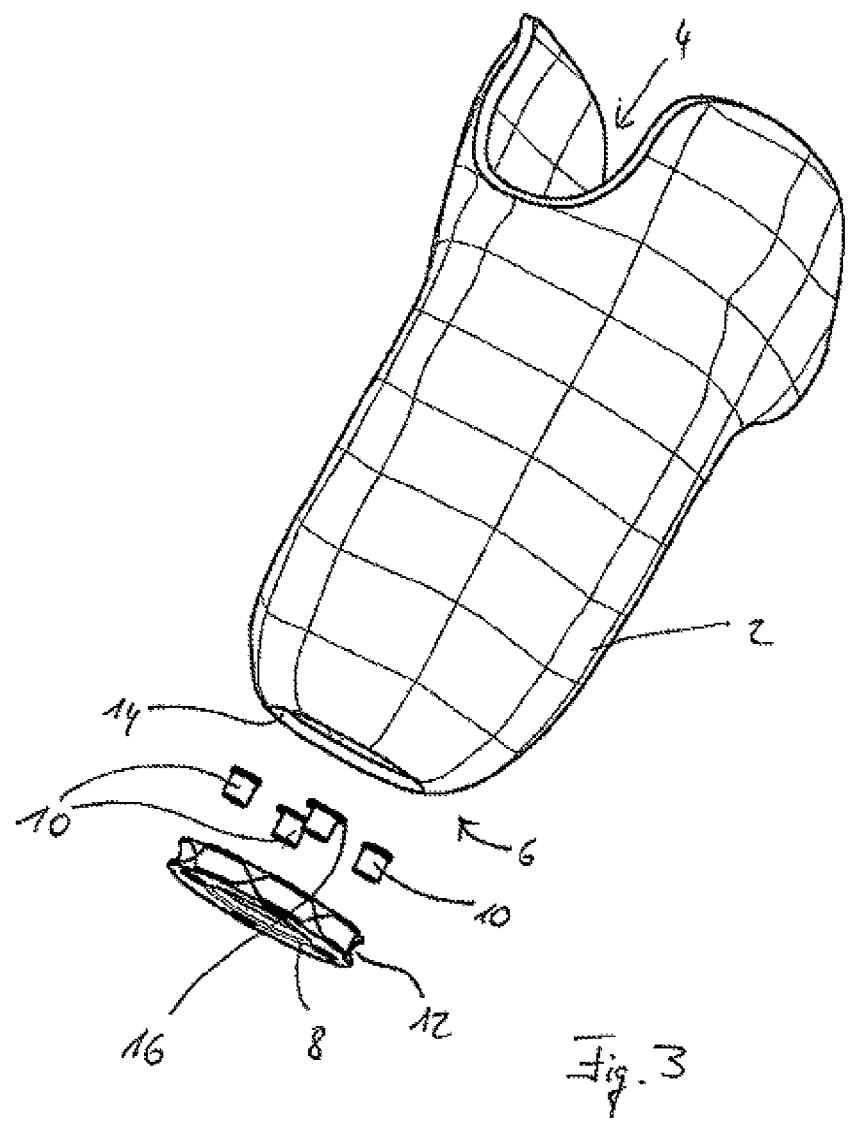
FIG. 3 shows a socket system according to a further illustrative embodiment of the present invention, in an exploded view.

FIG. 3 shows the view from FIG. 1 in an exploded view. A groove 12, which is relatively shallow in FIG. 3, can be seen extending around the periphery of the adapter element 8, into which groove 12 there engages an edge 14 provided at the distal end 6 of the prosthesis socket 2. This creates a form-fit connection between the adapter element 8 and the prosthesis socket 2. It will also be noted that, at their end facing toward the proximal opening 4 of the prosthesis socket 2, the four threaded inserts 10 each have a small flange 16, which reliably prevents removal of the threaded inserts 10 from the adapter element 8 in the distal direction, i.e. downward in FIG. 3.

FIG. 4 shows an enlarged view of the adapter element 8. FIG. 5 shows the view from FIG. 4 in an exploded view. It shows the adapter element 8 with the peripheral groove 12 into which the edge 14 of the prosthesis socket 2 engages in order to produce a form-fit connection. FIG. 5 shows four recesses 18 into which the four threaded inserts 10 are inserted. At the upper end of the threaded inserts 10 in FIG. 5, the flange 16 can be clearly seen with which the threaded inserts 10 each bear on a projection 20 provided in each recess 18. This makes it impossible for the threaded inserts 10 to fall down toward the left in FIG. 5, i.e. in the distal direction. The threaded inserts 10 each have a central bore 22 which, in the illustrative embodiment shown, is a through-opening and is provided with an inner thread. Into this can be inserted screw connections, by means of which distal prosthetic elements can be connected to the adapter element 8. Of course, it is equally conceivable that the central bores 22 are not through-openings but instead are accessible only from the underside (not shown in FIG. 5) of the threaded inserts 10.

In this embodiment, it is possible for the threaded inserts 10 to have already been introduced into the adapter element 8 before the adapter element 8 is connected to the prosthesis socket 2. As an alternative to this, it is of course also possible for the threaded inserts 10 to be introduced following the insertion of the adapter element 8 into the prosthesis socket 2 and, in particular, after the curing of the first fiber-reinforced plastic that forms the prosthesis socket 2.

The threaded inserts 10 are advantageously produced from a material not sensitive to water, for example stainless steel. It is true that the latter has a coefficient of thermal expansion different than the surrounding second fiber-reinforced plastic of the adapter element 8, such that different thermal expansion takes place by heating during the curing of the fiber-reinforced plastic. However, this is so slight, because of the very small dimensions of the threaded inserts, that no appreciable play occurs. However, if one wanted to avoid even such little play as this, it is recommended that the threaded inserts be introduced only after the fiber-reinforced plastics have cured, and therefore only after the adapter element 8 has been inserted into the prosthesis socket 2. This is possible, for example, by introducing the recesses 18 with the projections 20 only after the fiber-reinforced plastics have cured and therefore after the connection of the adapter element 8 to the prosthesis socket 2.

FIG. 6 shows a prosthesis according to an illustrative embodiment of the present invention. The socket system 1 can be seen with the prosthesis socket 2 and the proximal opening 4. The adapter element 8, on which the peripheral groove 12 can be seen, is arranged at the distal end 6 of the prosthesis socket 2. On the distal side of the adapter element 8, a prosthetic element is arranged which comprises a tube element 24, which is secured at its proximal end 26 to the adapter element 8. The tube element 24 can be longitudinally adjustable for example, in order to be able to be used on amputation stumps of differing length. At the distal end 28, lying opposite the proximal end 26, there is a prosthetic foot 30.

LIST OF REFERENCE SIGNS 1 socket system
2 prosthesis socket
4 proximal opening
6 distal end
8 adapter element
10 threaded insert
12 groove
14 edge
16 flange
18 recess
20 projection
22 bore
24 tube element
26 proximal end
28 distal end
30 prosthetic foot

The invention claimed is:

1. A socket system for a prosthesis, the socket system comprising:
a prosthesis socket which has a proximal opening for receiving an amputation stump, and a distal end, the prosthesis socket comprising a first fiber-reinforced plastic;
an adapter element positioned at the distal end of the prosthesis socket and configured to connect to a distal prosthetic element, the adapter element having a main body which comprises a second fiber-reinforced plastic, the fibers of the second reinforced plastic being substantially distributed throughout the main body except optionally for a core of the main body, the main body including a groove that extends around a periphery of the adapter element and extends only partially radially inward from a peripheral edge of the adapter, a portion of the prosthesis socket extending into the groove to provide a form fit between the prosthesis socket and the adapter element;

wherein at least one of the first fiber-reinforced plastic and the second fiber-reinforced plastic is a glass-fiber-reinforced or carbon-fiber-reinforced plastic.

2. The socket system as claimed in claim 1, wherein the first fiber-reinforced plastic and the second fiber-reinforced plastic contain fibers of the same material.

3. The socket system as claimed in claim 1, wherein the adapter element is connected to the prosthesis socket with at least one of cohesive material bonding and a form fit.

4. The socket system as claimed in claim 1, wherein at least one threaded insert is arranged in the adapter element.

5. The socket system as claimed in claim 4, wherein the at least one threaded insert is made of a material not sensitive to water.

6. The socket system as claimed in claim 1, wherein the main body of the adapter element is designed as a fiber-reinforced injection-molded part.

7. A prosthesis with a socket system as claimed in claim 1.

8. A socket system for a prosthesis, said socket system comprising:

a prosthesis socket having a proximal opening configured to receive an amputation stump, and a distal end, the prosthesis socket comprising a first fiber-reinforced plastic;

an adapter element positioned at the distal end of the prosthesis socket and configured to be secured to a distal prosthetic element, the adapter element having a main body comprising a second fiber-reinforced plastic;

a plurality of threaded inserts configured to be selectively engaged and disengaged in pass-through bores formed in the adapter element and configured to receive and threadably mate with threaded fasteners to releasably connect the adapter element to the distal prosthetic element;

wherein at least one of the first fiber-reinforced plastic and the second fiber-reinforced plastic is a glass-fiber-reinforced or carbon-fiber-reinforced plastic.

9. The socket system as claimed in claim 8, wherein the adapter element is connected to the prosthesis socket with at least one of a cohesive material bonding and a form fit.

10. The socket system as claimed in claim 8, further comprising at least one threaded insert arranged in the adapter element.

11. The socket system as claimed in claim 10, wherein the at least one threaded insert comprises stainless steel.

12. The socket system as claimed in claim 8, wherein the main body of the adapter element is formed as a fiber-reinforced injection-molded part.

13. A prosthesis having the socket system as claimed in claim 8.

* * * * *